United States Patent
Van De Pas et al.

(10) Patent No.: US 11,819,291 B2
(45) Date of Patent: Nov. 21, 2023

(54) INTERVENTIONAL DEVICE WITH PVDF ULTRASOUND DETECTOR

(71) Applicant: KONINKLIJKE PHILIPS N.V., Eindhoven (NL)

(72) Inventors: Stefan Van De Pas, Herten (NL); Willem-Jan Arend De Wijs, Oss (NL); Cornelis Gerardus Visser, Eindhoven (NL); Renate Wilhelmina Boekhoven, Eindhoven (NL); Ameet Kumar Jain, Boston, MA (US); Ramon Quido Erkamp, Swampscott, MA (US); Francois Guy Gerard Vignon, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 41 days.

(21) Appl. No.: 17/266,548

(22) PCT Filed: Aug. 2, 2019

(86) PCT No.: PCT/EP2019/070885
§ 371 (c)(1),
(2) Date: Feb. 5, 2021

(87) PCT Pub. No.: WO2020/030546
PCT Pub. Date: Feb. 13, 2020

(65) Prior Publication Data
US 2021/0315644 A1    Oct. 14, 2021

Related U.S. Application Data

(60) Provisional application No. 62/716,131, filed on Aug. 8, 2018.

(30) Foreign Application Priority Data

Oct. 5, 2018  (EP) ..................................... 18198769

(51) Int. Cl.
| | | |
|---|---|---|
| A61B 34/20 | (2016.01) | |
| A61B 90/00 | (2016.01) | |
| B06B 1/06 | (2006.01) | |

(52) U.S. Cl.
CPC .............. A61B 34/20 (2016.02); A61B 90/37 (2016.02); B06B 1/0688 (2013.01); *A61B 2034/2063* (2016.02); *A61B 2034/2065* (2016.02); *A61B 2090/3786* (2016.02)

(58) Field of Classification Search
CPC . A61B 34/20; A61B 90/37; A61B 2034/2063; A61B 2034/2065;
(Continued)

(56) References Cited

U.S. PATENT DOCUMENTS

| | | | |
|---|---|---|---|
| 5,070,882 A | 12/1991 | Bui | |
| 6,217,518 B1 * | 4/2001 | Holdaway | ............ A61B 5/6848 600/443 |

(Continued)

FOREIGN PATENT DOCUMENTS

WO    2017102338 A1    6/2017

OTHER PUBLICATIONS

International Search Report and Written Opinion of PCT/EP2019/070885, dated Sep. 13, 2019.

(Continued)

*Primary Examiner* — Joel Lamprecht
*Assistant Examiner* — Nyrobi Celestine

(57) ABSTRACT

An interventional device includes an elongate shaft (101) with a longitudinal axis (A-A'), and an ultrasound detector (102). The ultrasound detector (102) comprises a PVDF homopolymer foil strip (103). The foil strip (103) is wrapped around the longitudinal axis (A-A') of the elongate shaft (Continued)

(101) to provide a band having an axial length (L) along the longitudinal axis (A-A'). The axial length (L) is in the range 80-120 microns.

10 Claims, 4 Drawing Sheets

(58) Field of Classification Search
CPC .... A61B 2017/3413; A61B 2090/3929; A61B 17/3403; A61B 8/12; A61B 8/0841; A61B 10/0233; B06B 1/0688
See application file for complete search history.

(56) References Cited

U.S. PATENT DOCUMENTS

| | | | |
|---|---|---|---|
| 2002/0173720 A1* | 11/2002 | Seo | A61B 8/14 |
| | | | 600/437 |
| 2009/0076594 A1* | 3/2009 | Sabaria | A61L 31/148 |
| | | | 623/1.34 |
| 2010/0268014 A1* | 10/2010 | Pitman | A61N 5/1049 |
| | | | 600/7 |
| 2015/0327997 A1* | 11/2015 | Pollack | A61B 34/25 |
| | | | 623/2.11 |
| 2016/0367322 A1* | 12/2016 | Jain | G01S 15/899 |
| 2017/0027605 A1* | 2/2017 | Erkamp | A61B 8/5269 |
| 2017/0172544 A1* | 6/2017 | Erkamp | B06B 1/0688 |
| 2017/0172618 A1 | 6/2017 | Erkamp | |
| 2017/0258439 A1* | 9/2017 | Jasperson | A61B 8/445 |
| 2017/0360398 A1* | 12/2017 | Hamm | A61B 8/445 |
| 2018/0193000 A1* | 7/2018 | Shepard | G10K 11/343 |
| 2018/0207683 A1 | 7/2018 | De Wijs | |

OTHER PUBLICATIONS

Lu, Huanxiang et al "A New Sensor Technology for 2D Ultrasound-Guided Needle Tracking" MICCAI 2014, Part II, LNCS 8674, pp. 389-396.

* cited by examiner

INTERVENTIONAL DEVICE WITH PVDF ULTRASOUND DETECTOR

CROSS-REFERENCE TO PRIOR APPLICATIONS

This application is the U.S. National Phase application under 35 U.S.C. § 371 of International Application No. PCT/EP2019/070885, filed on Aug. 2, 2019, which claims the benefit of U.S. Provisional Patent Application Ser. No. 62/716,131, filed Aug. 8, 2018 and European Patent Application No. 18198769.4, filed on Oct. 5, 2018. These applications are hereby incorporated by reference herein.

FIELD OF THE INVENTION

The invention relates to an interventional device having a polyvinylidene fluoride, i.e. PVDF, ultrasound detector. The ultrasound detector may be used in various sensing applications in the medical field including position tracking. In one exemplary application the PVDF ultrasound detector may be used to track the position of the interventional device respective the ultrasound field of a beamforming ultrasound imaging probe.

BACKGROUND OF THE INVENTION

Interventional procedures in the medical field increasingly use ultrasound detectors to gain more information about a patient's anatomy. In this regard, ultrasound devices may be equipped with an ultrasound detector in sensing applications such as position tracking and blood flow sensing.

In one exemplary application described in more detail in document [1] "A New Sensor Technology for 2D Ultrasound-Guided Needle Tracking" by Huanxiang Lu, Junbo Li, Qiang Lu, Shyam Bharat, Ramon Erkamp, Bin Chen, Jeremy Drysdale, Francois Vignon, and Ameet Jain; P. Golland et al. (Eds.): MICCAI 2014, Part II, LNCS 8674, pp. 389-396, 2014, an ultrasound sensor is attached to a medical needle to track the position of the needle respective the ultrasound field of a beamforming ultrasound imaging probe. Performance results for two different materials are disclosed: dip-coated poly(vinylidene fluoride (VDF)-trifluoroethylene (TrFE)) co-polymer, and lead zirconate titanate, i.e. PZT.

A document US 2017/172618 A1 discloses a medical device that includes a conductive body including a surface and a sensor conformally formed on the surface and including a piezoelectric polymer formed about a portion of the surface and following a contour of the surface. The piezoelectric polymer is configured to generate or receive ultrasonic energy. Electrical connections conform to the surface and are connected to an electrode in contact with the piezoelectric polymer. The electrical connections provide connections to the piezo electric polymer and are electrically isolated from the conductive body over a portion of the surface.

Another document U.S. Pat. No. 5,070,882 A discloses an ultrasonic transducer for a catheter tip that has a thin strip of piezoelectric polymer film formed into a spiral ring and adhesively mounted on the support structure near the catheter tip. Electrical connection between the back face of the film and the support structure negative electrode is via capacitive coupling. Connection to the front face of the film is via a wire connected to the positive electrode of the catheter. A further embodiment suitable for a needle transducer is formed by coating the tip with a solution of PVDF co-polymer to form the actual transducer.

Another document WO 2017/102338 A1 relates to determining the rotation of an interventional device in an ultrasound field. An interventional device is provided that is suitable for being tracked in an ultrasound beam of a beamforming ultrasound imaging system by correlating transmitted ultrasound signals from the beamforming ultrasound imaging system as detected by ultrasound receivers attached to the interventional device with the beamforming beam sequence of the ultrasound signals. The interventional device includes a longitudinal axis, a first linear sensor array comprising a plurality of ultrasound receivers wherein each ultrasound receiver has a length and a width, and wherein the array extends along the width direction. Moreover the first linear sensor array is wrapped circumferentially around the interventional device with respect to the axis such that the length of each ultrasound receiver is arranged lengthwise with respect to the axis.

Despite this progress there remains room to provide an interventional device with an improved ultrasound detector in this and other medical application areas.

SUMMARY OF THE INVENTION

The present invention seeks to provide an interventional device with an improved ultrasound detector. Thereto an interventional device and an ultrasound-based position determination system are provided. The interventional device has an elongate shaft with a longitudinal axis. The interventional device has an ultrasound detector that includes a polyvinylidene fluoride, PVDF, homopolymer foil strip. The foil strip is wrapped around the longitudinal axis of the elongate shaft to provide a band having an axial length along the longitudinal axis. The axial length is in the range 80-120 microns.

The inventors have found that an axial length of PVDF homopolymer foil strip within this range provides an ultrasound detector that has a low variation in sensitivity with azimuthal angle. Moreover, such an axial length also results in high sensitivity at small azimuthal angles. In general, an ultrasound detector in the form of such a band might be expected to have negligible sensitivity at azimuthal angles of 0° and 180°, i.e. parallel to the longitudinal axis of the elongate shaft, and maximum sensitivity at a azimuthal angles of 90°, i.e. perpendicular to the elongate shaft. In general it may also be expected that the absolute sensitivity of an ultrasound detector in the form of such a band might scale linearly with the axial length of the band. Surprisingly, the inventors have found that an axial length in the range 80-120 microns exhibits both high sensitivity at small azimuthal angles and a low variation in sensitivity with azimuthal angle. Furthermore, an axial length in the range 80-120 microns has been found to provide adequate sensitivity to ultrasound.

In accordance with one aspect the foil strip has a thickness in the range 8.5-9.5 microns. Such a thickness provides an ultrasound detector with a high degree of flexibility, allowing the band to be wrapped around the longitudinal axis of the elongate shaft. Moreover, such a thickness can be reliably manufactured without defects.

In accordance with one aspect the elongate shaft has Birmingham Wire Gauge in the range 22 to 20. The ultrasound detector band is sufficiently flexible to be wrapped around a needle diameter with a Gauge in this range.

In accordance with one aspect an ultrasound-based position determination system includes the interventional device.

Further aspects are described with reference to the appended claims. Further advantages from the described invention will also be apparent to the skilled person.

DETAILED DESCRIPTION OF THE INVENTION

In order to illustrate the principles of the present invention an interventional device in the form of a medical needle is described with particular reference to an exemplary position tracking application in which the positon of an ultrasound detector on the needle is determined respective the ultrasound field of a beamforming ultrasound imaging probe. It is however to be appreciated that the invention may also be used in other medical application areas that employ ultrasound detectors such as blood flow sensing. The invention also finds application with other interventional devices than a medical needle, including without limitation a catheter, a guidewire, a biopsy device, a guidewire, a pacemaker lead, an intravenous line or a surgical tool in general. The interventional device may be used in a wide variety or medical procedures, for example from routine needle insertion for regional anesthesia, to biopsies and percutaneous ablation of cancer, and to more advanced interventional procedures.

Figure 1A:
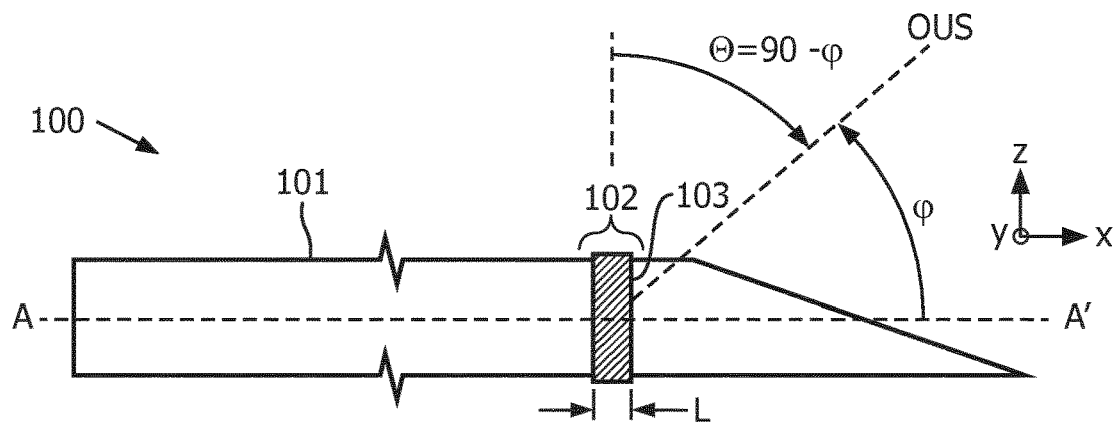
FIG. 1 illustrates orthogonal views of an interventional device 100 with an ultrasound detector 102 that includes a PVDF homopolymer foil strip 103.
Figure 1B:
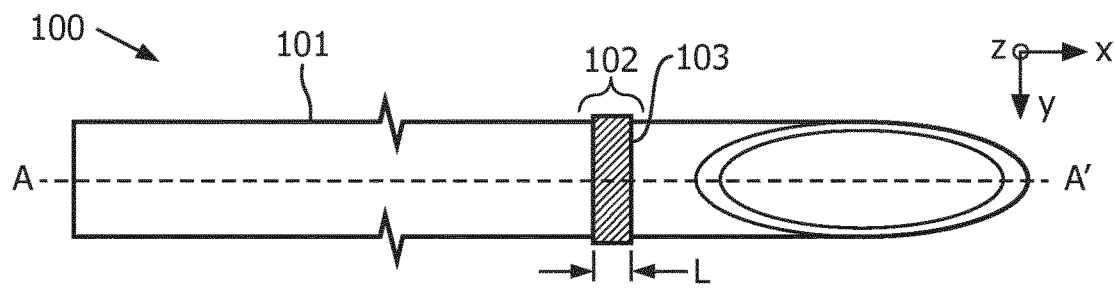

FIG. 1 illustrates orthogonal views of an interventional device 100 with an ultrasound detector 102 that includes a PVDF homopolymer foil strip 103. Interventional device 100 includes an elongate shaft 101 that has a longitudinal axis (A-A'), and ultrasound detector 102. Ultrasound detector 102 includes a PVDF homopolymer foil strip 103. Foil strip 103 is wrapped around longitudinal axis A-A' of elongate shaft 101 to provide a band having an axial length L along longitudinal axis A-A'. The band lies in a plane that is normal with respect to longitudinal axis A-A'. Moreover, axial length (L) is preferably in the range 80-120 microns.

As mentioned above, it has been found that an axial length of PVDF homopolymer foil strip within this range provides an ultrasound detector that has a low variation in sensitivity with azimuthal angle. High performance is also found within the narrower ranges of 80-110 microns, or 90-120 microns, or 90-110 microns. Moreover, such an axial length also results in high sensitivity at small azimuthal angles. Both results are somewhat surprising in view of the highly variable sensitivity performance results reported in [1] for ultrasound detectors that were made from different materials, i.e. PVDF co-polymer and PZT, and using different construction types, i.e. dip-coating.

Figure 2:
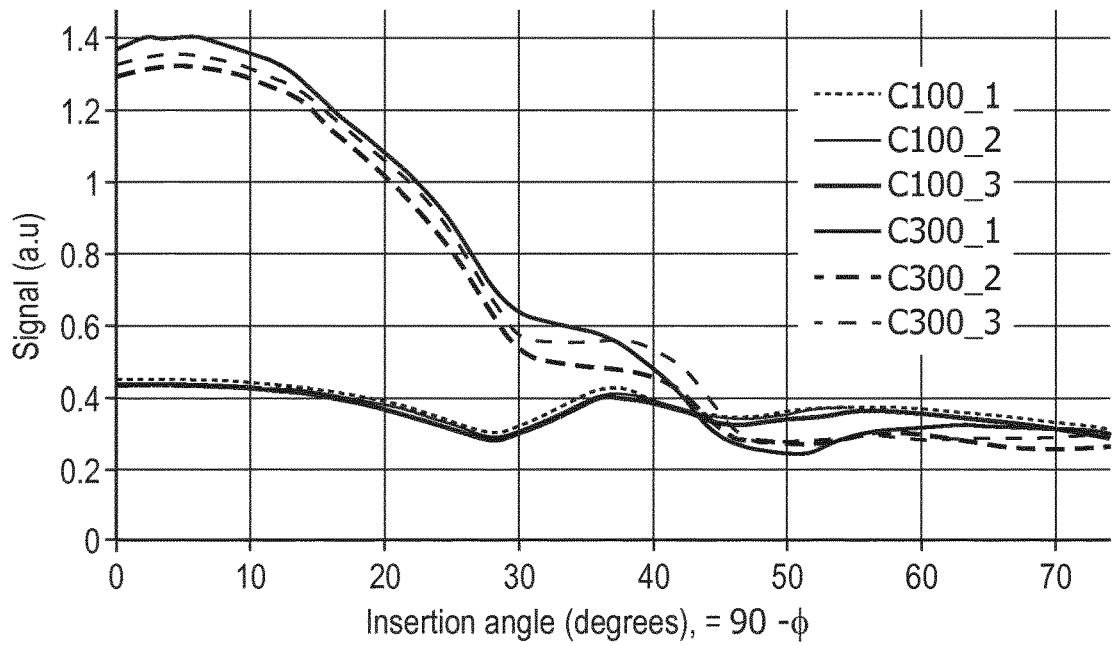
FIG. 2 illustrates the measured variation in detector sensitivity, Signal, with Insertion angle, 90°-Azimuthal angle ($\phi$), for three interventional devices 100 each having a PVDF homopolymer foil strip in the form of a band with an axial length L of 100 microns, C100-1, C100-2, C100-3, and three interventional devices 100 each having a PVDF homopolymer foil strip in the form of a band with an axial length L of 300 microns, C300-1, C300-2, C300-3.

FIG. 2 illustrates the measured variation in detector sensitivity, Signal, with Insertion angle, 90°-Azimuthal angle ($\phi$), for three interventional devices 100 each having a PVDF homopolymer foil strip in the form of a band with an axial length L of 100 microns, C100-1, C100-2, C100-3, and three interventional devices 100 each having a PVDF homopolymer foil strip in the form of a band with an axial length L of 300 microns, C300-1, C300-2, C300-3. Azimuthal angle $\phi$ as defined herein is illustrated in FIG. 1 as the angle formed between the zenith, i.e. a line parallel to longitudinal axis A-A' and pointing in the direction of the distal end of the interventional device, and the origin of the ultrasound source OUS, and which angle has an apex disposed at the center of the PVDF foil band. Insertion angle $\theta$ is defined as $\theta = 90 - \phi$, as illustrated in FIG. 1. The parameter Signal represents the detected signal normalized to its value at an azimuthal angle of 90°.

In general, an ultrasound detector in the form of such a band might be expected to have negligible sensitivity at azimuthal angles of 0° and 180°, i.e. parallel to the longitudinal axis A-A' of elongate shaft 101, and maximum sensitivity at a azimuthal angles of 90°, i.e. perpendicular to the elongate shaft. In general it may also be expected that the absolute sensitivity of an ultrasound detector in the form of such a band might scale linearly with the axial length of the band.

The three above trends are indeed observed in the measurements of FIG. 2. A maximum signal is measured at an insertion angle of 0° or an azimuthal angle of 90°, and the signal tends towards zero at incidence angles greater than 75°, i.e. at azimuthal angles less 15°. Moreover the maximum signal for the 300 micron axial length devices, C300-1, C300-2, C300-3, is approximately three times that of the 100 micron axial length devices, C100-1, C100-2, C100-3.

Surprisingly, as illustrated in FIG. 2 the measurements for the 100 micron axial length devices exhibit both high sensitivity at small azimuthal angles, in particular at insertion angles from 500-70°, and a low variation in sensitivity with azimuthal angle. Indeed the 100 micron axial length devices C100-1, C100-2, C100-3 exhibit even higher sensitivity at insertion angles from 500-700 than the 300 micron axial length devices C300-1, C300-2, C300-3. The variation with azimuthal angle for the 100 micron axial length devices C100-1, C100-2, C100-3 of approximately a factor of 1.5, is also much smaller than the variation with azimuthal angle for the 300 micron axial length devices C300-1, C300-2, C300-3 of approximately a factor of 5.4, within an insertion angle range of approximately 0°-70°.

This finding is highly significant for PVDF detectors formed in such a band. Having a small variation in sensitivity with azimuthal angle offers uniform signal to noise ratio performance, and may obviate the need for switchable amplifiers that might otherwise be needed provide this via an adjustable gain that depends on the detected signal level or on the azimuthal angle. Moreover, applications that use the detected signal strength to determine a sensor parameter such as range may benefit from the much flatter sensitivity profiles of the 100 micron devices illustrated in FIG. 2. Furthermore, a band having an axial length of 100 microns has been found to provide adequate sensitivity to ultrasound. Bands with significantly shorter axial lengths than this may result in a poor signal to noise ratio.

As mentioned above, foil strip 103 is made from a PVDF homopolymer. The term PVDF homopolymer as used herein refers to a polymer in which a single monomer, specifically, vinyldifluoride, i.e. VDF, is repeated to form the whole polymer. This term is used to distinguish from a copolymer, in which there are two monomers that form the polymer. This term is also used to distinguish from the term polymer blend, in which two different homopolymers are mixed in the melt. One exemplary supplier of PVDF homopolymer foil is Goodfellow, Cambridge, UK. Other similar PVDF homopolymer foils may likewise be used to provide foil strip 103. Foil strip 103 may optionally have a thickness in the range 8.5-9.5 microns. Such a thin layer offers a balance between high flexibility, particularly to allow for wrapping of foil strip 103 as a band around elongate shaft 101, and adequate signal strength. Thinner layers can be tricky to manufacture reliably. Moreover, whilst foil strip 103 may be used with a wide range of elongate shaft diameters, preferably elongate shaft 101 has a diameter that corresponds to a Birmingham Wire Gauge in the range 22 to 20; i.e. a nominal outer diameter of from 0.7176 millimeters to 0.9081 millimeters.

Figure 3A:
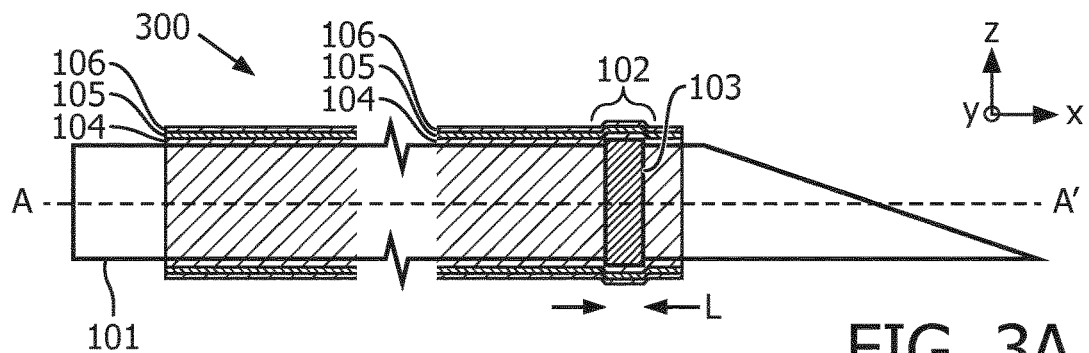
FIG. 3 illustrates orthogonal views of an interventional device 300 with an ultrasound detector 102 that includes homopolymer foil strip 103 formed from PVDF and electrical shield layer 105.
Figure 3B:
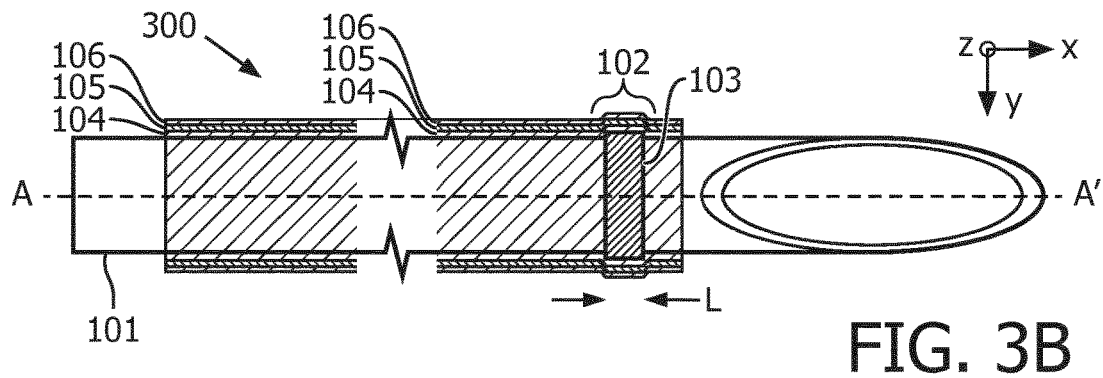

FIG. 3 illustrates orthogonal views of an interventional device 300 with an ultrasound detector 102 that includes homopolymer foil strip 103 formed from PVDF and electrical shield layer 105. Features in FIG. 3 with the same references as those in FIG. 1 refer to the same features. Electrical shield layer 105 may surround ultrasound detector 102 and/or any electrical conductors, not shown in FIG. 3A, connected thereto that may extend along elongate shaft 101, and thereby provide electrical shielding. Suitable materials for electrical shield layer 105 include metal foils such as copper, gold and so forth. Electrical insulator layer 104 may also, as illustrated in FIG. 3 be disposed between foil strip 103 and electrical shield layer 105. Electrical insulator layer 104 may in some implementations be used to electrically insulate foil strip 103 from electrical shield layer 105. Electrical insulator layer 104 may for example be formed from an insulator such as a polymer, for polyethylene terephthalate, PET, polyimide, PI, or polyamide, PA.

FIG. 3 also includes optional protective tube 106. Protective tube 106 may provide a sterilisable outer coating and/or reduce the ingress of moisture into the ultrasound detector. Protective tube 106 may also provide a smooth topology over the ultrasound detector and thereby provide for a smooth introduction of the interventional device into a body. Various materials are contemplated for use as protective tube 106. Heat-shrink materials are preferred in view of their benefit of reduced manufacturing complexity. Polyolefins and flouropolymers including PVDF, HDPE, LDPE, EMA are amongst the materials that are contemplated. Suppliers of suitable polyester PET materials for protective tube 106 include Nordson Medical, Colorado, USA and Raychem Corporation, USA.

Various techniques are contemplated to provide foil strip 103 on elongate shaft 101. These include wrapping foil strip 103 around elongate shaft 101 to provide a band; assembling a stack of layers on elongate shaft 101; or providing stack of pre-assembled layers and attaching this stack to the shaft. Electrical conductors may be subsequently connected to the foil strip, or these maybe incorporated within the layers. In respect of the exemplary pre-assembled stack configuration, FIG. 4 illustrates various views of an elongate stack 430 that includes first electrical conductor 111, second electrical conductor 112, first electrode 113 and second electrode 114. With reference to FIG. 5, which illustrates orthogonal views of an interventional device 100 in which ultrasound detector 102 is provided by elongate stack 430 that is wrapped in the form of a spiral around elongate shaft 101 of interventional device 100, elongate stack 430 may be attached to elongate shaft 101 to provide interventional device 100. Elongate shaft may for example be the shaft of a medical needle, as illustrated in FIG. 5, or indeed another the shaft of another medical device.

Figure 4A:
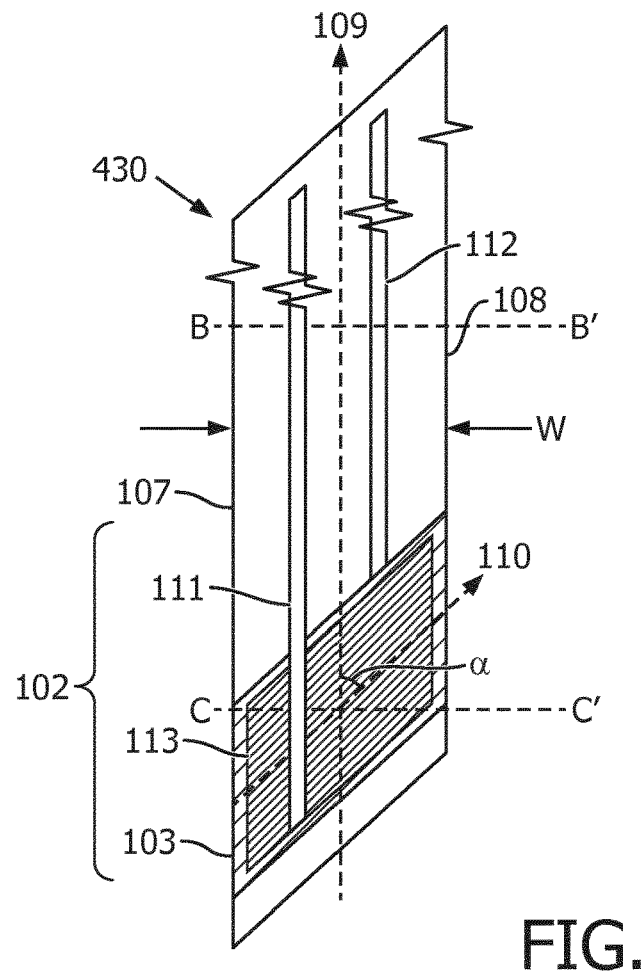
FIG. 4 illustrates various views of an elongate stack 430 that includes first electrical conductor 111, second electrical conductor 112, first electrode 113 and second electrode 114.
Figure 5A:
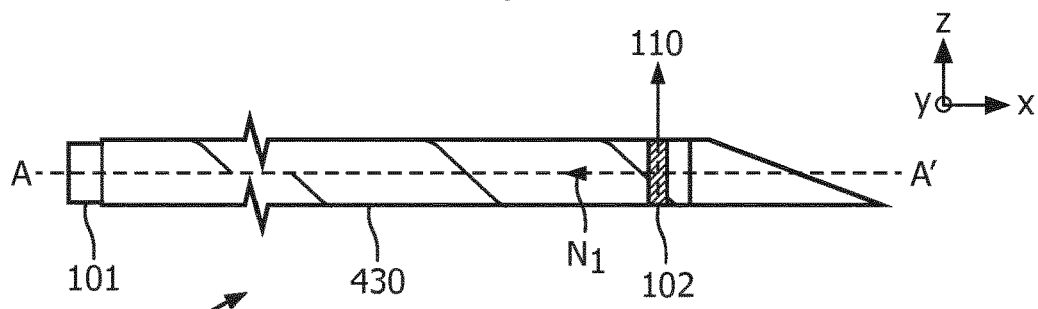
FIG. 5 illustrates orthogonal views of an interventional device 100 in which ultrasound detector 102 is provided by elongate stack 430 that is wrapped in the form of a spiral around elongate shaft 101 of interventional device 100.
Figure 5B:
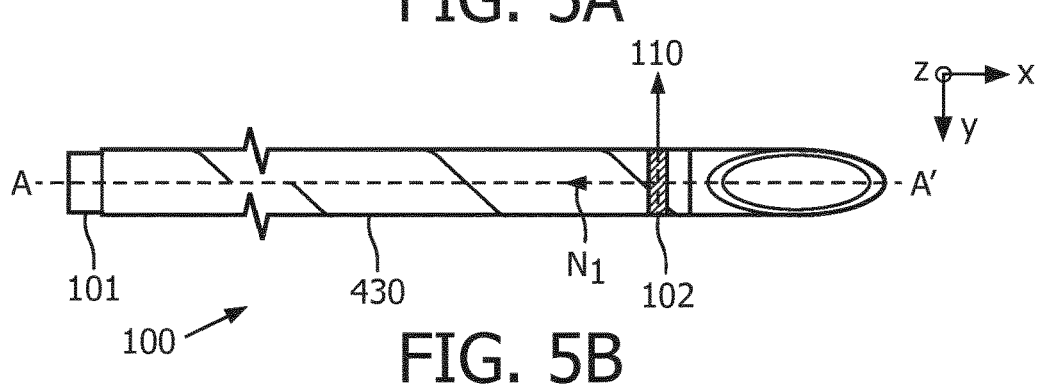

In FIG. 4A, it is noted that foil strip 103 is tilted with respect to the strip such that when wrapped around elongate axis 102, ultrasound detector 102 is provided in the form of a band that lies in a plane that is normal $N_1$ to longitudinal axis A-A', as illustrated in FIG. 5. In alternative attachment techniques, foil strip 103 may be arranged perpendicularly with respect to the strip such that when elongate stack 430 is attached lengthwise along longitudinal axis A-A' with electrical conductors 111, 112 parallel to along longitudinal axis A-A', ultrasound detector 102 is again provided in the form of a band.

Figure 4B:
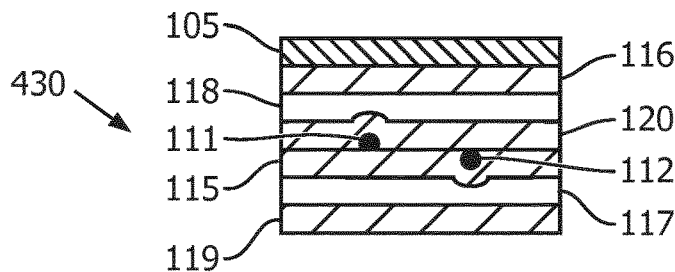
Figure 4C:
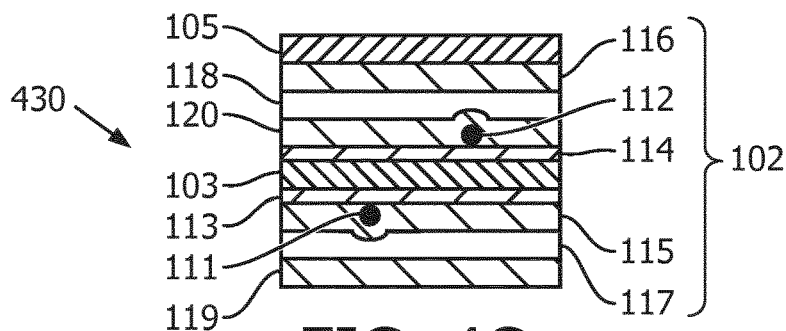
Figure 4D:
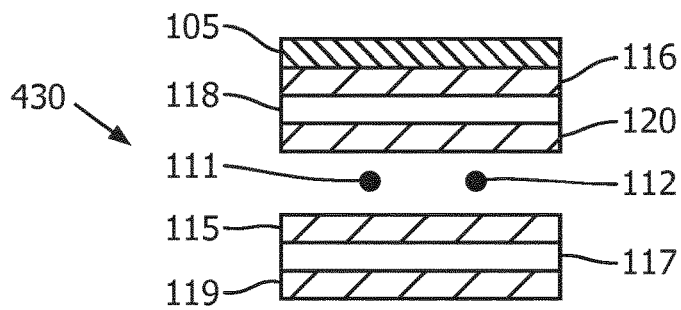
Figure 4E:
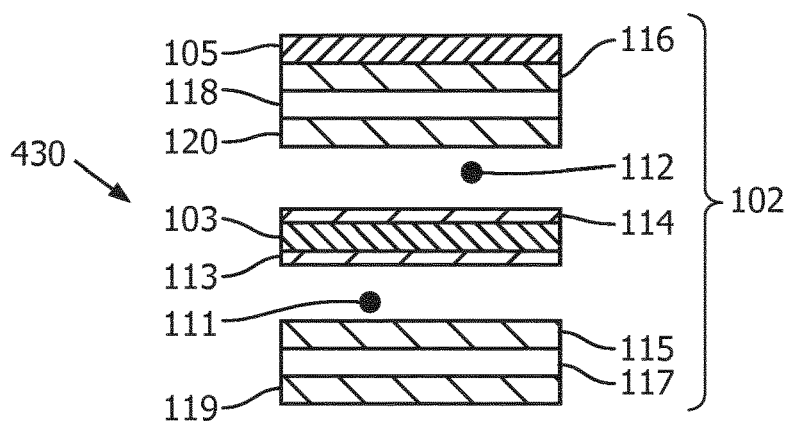

With reference to FIG. 4, elongate stack 430 is illustrated in plan view in FIG. 4A, and as sections through B-B' and C-C' in FIG. 4B and FIG. 4C, and exploded sections through B-B' and C-C' FIG. 4D and FIG. 4E. Elongate stack 430 includes foil strip 103, first electrical conductor 111, second electrical conductor 112, first polymer layer 117, and second polymer layer 118.

Polymer layers 117, 118 may for example be formed from materials such as Polyethylene terephthalate, PET, Polyimide, PI, or Polyamide, PA. Moreover, polymer layers 117, 118 may include an adhesive coating, optionally a pressure sensitive adhesive coating, on one or both of their surfaces, these being illustrated as adhesive layers 116, 120, 115, 119 in FIG. 4. The adhesives act to bond each of the layers together. Pressure sensitive adhesives are a class of materials that form an adhesive bond upon application of pressure. Suitable suppliers of pressure sensitive adhesives include the 3M Corporation, USA. PSA-coated polymer sheets, i.e. foils, may be used in particular. Polymer layers with PSA on one or both surfaces may be used. PSA-coated polymer sheets are typically provided with a removable release layer that is peeled away to reveal the adhesive coating and thereby protect the adhesive layer until its adhesive properties are required. The foils may be formed from a range of polymer materials, for example Polyethylene terephthalate, PET, Polyimides, PI, or Polyamides, PA. Typically the foils are formed from an electrically insulating material.

Optionally, elongate stack 430 may also include electrical shield layer 105 which, as described above, provides electrical shielding to ultrasound detector 102 and/or electrical conductors 111, 112.

Elongate stack 430 has a first edge 107 and an opposing second edge 108, the first edge 107 and the second edge 108 being separated by a width dimension W. First edge 107 and second edge 108 each extend along length direction 109 of elongate stack 430. Foil strip 103 extends along a detector direction 110 that forms an acute angle α with respect to the length direction 109 of elongate stack 430.

Optionally, width dimension W in FIG. 4 may be defined such that adjacent first and second edges 107, 108 of consecutive turns of the spiral abut or overlap one another, or are separated by a gap.

In order for consecutive turns of the spiral to abut, i.e. just touch, one another, the following equation should be satisfied:

$$W = \pi \cdot D \cdot \sin(\alpha) \quad \text{Equation 1}$$

Wherein α is the acute angle defined by detector direction 110 with respect to length direction 109, and D is the diameter of elongate shaft 101. By arranging that W exceeds the above value, consecutive turns of the spiral overlap one another. Likewise by arranging that W is less than this value a gap may be provided between consecutive turns of the spiral.

As described above, in this implementation, elongate stack 430 is wrapped in the form of a spiral around elongate shaft 101 such that foil strip 103 provides the band.

The spiral wrapping of FIG. 5 for the elongate stack 430 in FIG. 4 provides a convenient method of attaching ultrasound detector 102 to elongate shaft 101. The interventional device may for example be rolled across elongate stack 430 and attached to the interventional device by means of an adhesive layer 119. The abutting or overlapping adjacent turns act to provide, respectively, a smooth outer surface to interventional device 110 and thereby lower resistance to insertion in a body, and avoid the exposure of material underlying wrapped elongate stack 430.

With further reference to FIG. 4C in particular, foil strip 103, which may be attached to elongate shaft 101, includes a first surface and a second surface. Ultrasound detector 102 further comprises first electrical conductor 111 and second electrical conductor 112. First electrical conductor 111 is in electrical contact with the first surface of the foil strip 103, and second electrical conductor 112 is in electrical contact with the second surface of the foil strip 103. Moreover, when attached to elongate shaft 101 as illustrated in FIG. 5, first electrical conductor 111 and second electrical conductor 112 each extend along elongate shaft 101 for making electrical contact with ultrasound detector 102 at an axially-separated position along elongate shaft 101 with respect to ultrasound detector 102.

Ultrasound detector 102 in FIG. 4C also includes first polymer layer 117 and second polymer layer 118. Foil strip 103 and first electrical conductor 111 and second electrical conductor 112 are sandwiched between first polymer layer 117 and second polymer layer 118.

Ultrasound detector 102 in FIG. 4C may also include optional electrical shield layer 105. Electrical shield layer 105 is disposed radially outwards of the first polymer layer 117 and the second polymer layer 118 with respect to the longitudinal axis A-A' such that at least along the axial length L of the band, the electrical shield surrounds the foil strip 103, as illustrated in FIG. 3A. Consequently electrical shield layer 105 extends along at least a portion of the elongate shaft 101. Moreover, as illustrated in FIG. 3, along the at least a portion of elongate shaft 101, electrical shield layer 105 may surround first electrical conductor 111 and second electrical conductor 112 for electrically shielding first electrical conductor 111 and second electrical conductor 112. It is noted that whilst in FIG. 3A, electrical conductors 111, 112 are surrounded in this way by electrical shield 105 for a substantial portion of the length of elongate shaft 101, there may be a gap in such electrical shield for making external electrical contact with the electrical conductors.

Optionally, in order to maintain a low insertion resistance, preferably the ultrasound detector 102 in FIG. 4C has a thickness in the range 10-100 microns, this being measured in a radial direction with respect to longitudinal axis A-A' of elongate shaft 101. A thickness in the range 10-80 microns offers improved performance. Significantly thinner ultrasound detectors than 10 microns become increasingly hard to fabricate.

As mentioned above, in one exemplary implementation, the interventional devices described herein may be used in an ultrasound-based tracking application. In this implementation, ultrasound detector may 102 may be configured to detect ultrasound signals emitted by a beamforming ultrasound imaging probe and the position of the ultrasound detector may be determined based on the detected ultrasound signals. Thereto, FIG. 6 illustrates an exemplary ultrasound-based position determination system 600 that includes interventional device 100.

Figure 6:
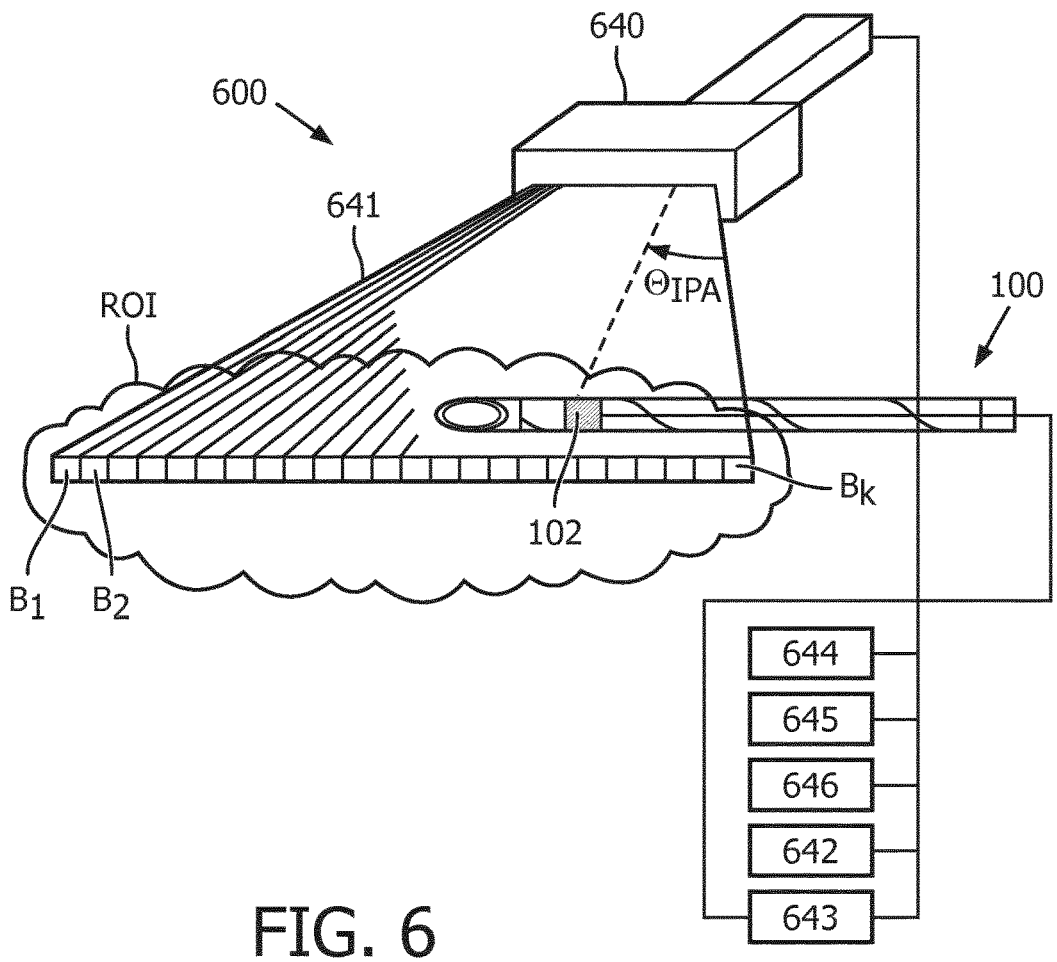
FIG. 6 illustrates an exemplary ultrasound-based position determination system 600 that includes interventional device 100.

With reference to FIG. 6, ultrasound-based position determination system 600 includes interventional device 100, beamforming ultrasound imaging probe 640, image reconstruction unit 642 and position determination unit 643. Display 644, imaging system interface 645, and imaging system processor 646 may optionally also be included. Beamforming ultrasound imaging probe 640 is configured to generate ultrasound field 641. Image reconstruction unit 642 is configured to provide a reconstructed ultrasound image corresponding to ultrasound field 641 of beamforming ultrasound imaging probe 640. Position determination unit 643 is configured to compute a position of ultrasound detector 102 of interventional device 100 respective ultrasound field 641 based on ultrasound signals transmitted between the beamforming ultrasound imaging probe 640 and the ultrasound detector 102, and to provide an icon in the reconstructed ultrasound image based on the computed position of ultrasound detector 102. Imaging system processor 646, imaging system interface 645 and display 644 are also shown in FIG. 6. Links between the various units illustrate their respective communication links.

Together, units 640, 642, 644, 645 and 646 form a conventional ultrasound imaging system. The units 642, 644, 645 and 646 are conventionally located in a console that is in wired or wireless communication with beamforming ultrasound imaging probe 640. Some of units 642, 644, 645 and 646 may alternatively be incorporated within beamforming ultrasound imaging probe 640 as for example in the Philips Lumify ultrasound imaging system. Beamforming ultrasound imaging probe 640 generates ultrasound field 641. In FIG. 6, a 2D beamforming ultrasound imaging probe 640 is illustrated that includes a linear ultrasound transceiver array that transmits and receives ultrasound energy within an ultrasound field 641 which intercepts region of interest ROI. The ultrasound field is fan-shaped in FIG. 6 and includes multiple ultrasound beams $B_{1 \ldots k}$ that together provide the illustrated image plane. Note that whilst FIG. 6 illustrates a fan-shaped beam the invention is not limited to use with a particular shape of ultrasound field or indeed to a planar ultrasound field. Beamforming ultrasound imaging probe 640 may also include electronic driver and receiver circuitry, not shown, that is configured to amplify and/or to adjust the phase of signals it transmits or receives in order to generate and detect ultrasound signals in ultrasound beams $B_{1 \ldots k}$.

In-use the above-described conventional ultrasound imaging system is operated in the following way. An operator may plan an ultrasound procedure via imaging system interface 645. Once an operating procedure is selected, imaging system interface 645 triggers imaging system processor 646 to execute application-specific programs that generate and interpret the signals transmitted to and detected by beamforming ultrasound imaging probe 640. A memory, not shown, may be used to store such programs. The memory may for example store ultrasound beam control software that is configured to control the sequence of ultrasound signals transmitted by and/or received by beamforming ultrasound imaging probe 640. Image reconstruction unit 642 provides a reconstructed ultrasound image corresponding to ultrasound field 641 of beamforming ultrasound imaging probe 640. Image reconstruction unit 642 thus provides an image corresponding to the image plane defined by ultrasound field 641 and which intercepts region of interest ROI. The function of image reconstruction unit 642 may alternatively be carried out by imaging system processor 646. The image may subsequently be displayed on display 644. The reconstructed image may for example be an ultrasound Brightness-mode "B-mode" image, otherwise known as a "2D mode" image, a "C-mode" image or a Doppler mode image, or indeed any ultrasound image.

Also shown in FIG. 6 is interventional device 100, exemplified by a medical needle, which includes ultrasound detector 102. In this exemplary application, interventional device 102, or more specifically ultrasound detector 102 disposed thereon, may be tracked respective ultrasound field 641 based on signals provided by position determination unit 643. Position determination unit is in communication with units 640, 642, 644, 645 and 646, i.e. the conventional ultrasound imaging system, as illustrated by the interconnecting links. Position determination unit 643 is also in communication with ultrasound detector 102, which communication may for example be wired or wireless. The function of position determination unit 643 may in some implementations be carried out by a processor of the conventional ultrasound imaging system.

In-use, the position of ultrasound detector 102 is computed respective ultrasound field 641 by position determination unit 643 based on ultrasound signals transmitted between beamforming ultrasound imaging probe 640 and ultrasound detector 102. Ultrasound detector 102 detects ultrasound signals corresponding to beams $B_{1\ldots k}$. Position determination unit 643 identifies the position of ultrasound detector 102 based on i) the amplitudes of the ultrasound signals corresponding to each beam $B_{1\ldots k}$ that are detected by ultrasound detector 102, and based on ii) the time delay, i.e. time of flight, between emission of each beam $B_{1\ldots k}$ and its detection by ultrasound detector 102. Position determination unit 643 subsequently provides an icon in the reconstructed ultrasound image based on the computed position of ultrasound detector 102. The icon may for example indicate the computed position of ultrasound detector 102. The icon may optionally also indicate a range of positions within which a portion of the interventional device, e.g. its distal end, may lie. More specifically the position is computed by finding the best fit position of ultrasound detector 102 respective ultrasound field 731 based on the detected ultrasound signals.

This may be illustrated as follows. When ultrasound detector 102 is in the vicinity of ultrasound field 641, ultrasound signals from the nearest of beams $B_{1\ldots k}$ to the detector will be detected with a relatively larger amplitude whereas more distant beams will be detected with relatively smaller amplitudes. Typically the beam that is detected with the largest amplitude is identified as the one that is closest to ultrasound detector 102. This beam defines the in-plane angle $\theta_{IPA}$ between beamforming ultrasound imaging probe 640 and ultrasound detector 102. The corresponding range depends upon the time delay, i.e. the time of flight, between the emission of the largest-amplitude beam $B_{1\ldots k}$ and its subsequent detection. If desired, the range may thus be determined by multiplying the time delay by the speed of ultrasound propagation. Thus, the time of flight and corresponding in-plane angle $\theta_{IPA}$ of the beam detected with the largest amplitude can be used to identify the best-fit position of ultrasound detector 102 respective ultrasound field 641.

In the above-described ultrasound-based position determination system 640 the dependence of the sensitivity profile of ultrasound detector 102, or more specifically its absolute value and/or dependence on azimuthal angle of the interventional device, may impact its computed position respective ultrasound field 641. Thereto, the use of the above-described interventional device has the benefits of improved reliability and sensitivity. Indeed, when in-use in such an application the insertion angle of an interventional device is frequently around 500 or more. The beamforming ultrasound imaging probe is in such applications disposed on the surface of the body and a needle bearing the ultrasound detector is often inserted from a position to the side of the imaging probe and into its imaging plane. The flatter sensitivity curve of the ultrasound detector represented in FIG. 2, and also its high value that are provided by the PVDF homopolymer foil strip at these insertion angles, thus provides significant performance advantages in system 640.

Whilst reference has been made above to a planar ultrasound imaging probe it is to be appreciated that the exemplified beamforming ultrasound imaging probe 640 is only one example of a beamforming ultrasound imaging probe in which interventional device 100 may be used. Interventional device 100 also finds application in ultrasound-based position determination systems that include other types of 2D or 3D beamforming ultrasound imaging probes. These may include for example a "TRUS" transrectal ultrasonography probe, an "IVUS" intravascular ultrasound probe, a "TEE" transesophageal probe, a "TTE" transthoracic probe, a "TNE" transnasal probe, an "ICE" intracardiac probe. Moreover, it is to be appreciated that interventional device 100 also finds application in other ultrasound sensing applications in the medical field beyond position tracking.

In summary, an interventional device that includes an elongate shaft and an ultrasound detector 102 has been described. The elongate shaft has a longitudinal axis. The ultrasound detector comprises a PVDF homopolymer foil strip. The foil strip is wrapped around the longitudinal axis of the elongate shaft to provide a band having an axial length along the longitudinal axis. The axial length is in the range 80-120 microns.

Various embodiments and options have been described in relation to the interventional device, and it is noted that the various embodiments may be combined to achieve further advantageous effects. Any reference signs in the claims should not be construed as limiting the scope of the invention.

The invention claimed is:

1. An interventional device comprising:
   an elongated shaft having a longitudinal axis; and
   an ultrasound detector comprising a polyvinylidene fluoride (PVDF) homopolymer foil strip,
   wherein the PVDF homopolymer foil strip is wrapped around the longitudinal axis of the elongated shaft in a form of a band having an axial length along the longitudinal axis, and
   wherein the axial length of the PVDF homopolymer foil strip is in a range of 80-120 microns, such that the ultrasound detector exhibits high sensitivity at small azimuthal angles and low variation in sensitivity with respect to variation in azimuthal angle.

2. The interventional device according to claim 1, wherein the PVDF homopolymer foil strip has a thickness in a range of 8.5-9.5 microns.

3. The interventional device according to claim 1, wherein the elongated shaft has an inner diameter or an outer diameter that corresponds to a Birmingham Wire Gauge in a range of 22 to 20.

4. The interventional device according to claim 1,
wherein the PVDF homopolymer foil strip includes a first surface and a second surface,
wherein the ultrasound detector further comprises a first electrical conductor and a second electrical conductor,
wherein the first electrical conductor is in electrical contact with the first surface of the PVDF homopolymer foil strip,
wherein the second electrical conductor is in electrical contact with the second surface of the PVDF homopolymer foil strip, and
wherein the first electrical conductor and the second electrical conductor each extend along the elongated shaft for making electrical contact with the ultrasound detector at an axially-separated position along the elongated shaft with respect to the ultrasound detector.

5. The interventional device according to claim 4,
wherein the ultrasound detector further comprises a first polymer layer and a second polymer layer, and
wherein the PVDF homopolymer foil strip and the first electrical conductor and the second electrical conductor are interposed between the first polymer layer and the second polymer layer.

6. The interventional device according to claim 5,
wherein the ultrasound detector further comprises an electrical shield layer, and
wherein the electrical shield layer is disposed radially outwards of the first polymer layer and the second polymer layer with respect to the longitudinal axis such that at least along the axial length of the band, the electrical shield layer surrounds the PVDF homopolymer foil strip.

7. The interventional device according to claim 6,
wherein the electrical shield layer extends along at least a portion of the elongated shaft, and
wherein along the at least a portion of the elongated shaft, the electrical shield layer surrounds the first electrical conductor and the second electrical conductor for electrically shielding the first electrical conductor and the second electrical conductor.

8. The interventional device according to claim 7, wherein the ultrasound detector has a thickness in a range of 10-100 microns in a radial direction with respect to the longitudinal axis.

9. The interventional device according to claim 5,
wherein the ultrasound detector is provided by an elongated stack, the elongated stack comprising:
the PVDF homopolymer foil strip;
the first electrical conductor;
the second electrical conductor;
the first polymer layer;
the second polymer layer,
wherein the elongated stack has a first edge and an opposing second edge, the first edge and the opposing second edge being separated by a width dimension, and the first edge and the second edge each extending along a length direction of the elongated stack,
wherein the PVDF homopolymer foil strip extends along a detector direction that forms an acute angle with respect to the length direction of the elongated stack, and
wherein the elongated stack is wrapped in a form of a spiral around the elongated shaft such that the PVDF homopolymer foil strip provides the band.

10. An ultrasound-based position determination system comprising:
the interventional device according to claim 1;
a beamforming ultrasound imaging probe configured to generate an ultrasound field;
an image reconstruction processor configured to provide a reconstructed ultrasound image corresponding to the ultrasound field of the beamforming ultrasound imaging probe; and
a position determination processor configured to compute a position of the ultrasound detector of the interventional device respective the ultrasound field based on ultrasound signals transmitted between the beamforming ultrasound imaging probe and the ultrasound detector, and to provide an icon in the reconstructed ultrasound image based on the computed position of the ultrasound detector.

* * * * *